United States Patent
Landry et al.

(10) Patent No.: US 11,571,238 B2
(45) Date of Patent: Feb. 7, 2023

(54) ENDARTERECTOMY DEVICE

(71) Applicant: Oregon Health & Science University, Portland, OR (US)

(72) Inventors: Gregory Landry, Portland, OR (US); Stevan Wittenbrock, Portland, OR (US); Daniel R. Baker, Seattle, WA (US); Christopher John Jensen, Beaverton, OR (US)

(73) Assignee: Oregon Health & Science University, Portland, OR (US)

(*) Notice: Subject to any disclaimer, the term of this patent is extended or adjusted under 35 U.S.C. 154(b) by 503 days.

(21) Appl. No.: 16/833,231

(22) Filed: Mar. 27, 2020

(65) Prior Publication Data
US 2020/0315649 A1   Oct. 8, 2020

Related U.S. Application Data

(60) Provisional application No. 62/824,896, filed on Mar. 27, 2019.

(51) Int. Cl.
*A61B 17/221* (2006.01)
*A61B 17/3207* (2006.01)
(Continued)

(52) U.S. Cl.
CPC .......... *A61B 17/3207* (2013.01); *A61B 90/37* (2016.02); *A61B 17/32056* (2013.01); *A61B 2017/00398* (2013.01); *A61B 2017/00734* (2013.01); *A61B 2017/00867* (2013.01); *A61B 2017/2212* (2013.01); *A61B 2017/2215* (2013.01); *A61B 2017/2217* (2013.01); *A61B 2017/320741* (2013.01); *A61B 2018/141* (2013.01); *A61B 2018/1407* (2013.01); *A61B 2090/0811* (2016.02); *A61B 2090/376* (2016.02)

(58) Field of Classification Search
CPC .......... A61B 17/3207; A61B 17/32056; A61B 2090/0811; A61B 17/221; A61B 2017/2212; A61B 2017/2215; A61B 2017/2217; A61B 2018/1407; A61B 2018/141
See application file for complete search history.

(56) References Cited

U.S. PATENT DOCUMENTS 6,152,936 A * 11/2000 Christy ............ A61B 17/12013
606/139
2004/0242960 A1* 12/2004 Orban, III .............. A61B 10/06
600/106
(Continued)

*Primary Examiner* — Shaun L David
*Assistant Examiner* — Mitchell Brian Hoag

(57) ABSTRACT

An endarterectomy device configured to remove plaque from an occluded artery is disclosed. The endarterectomy device uses an adjustable wire loop end effector to establish and advance a dissection plane in the subadventitial space of the artery. The endarterectomy device is passed down the length of an artery in the subadventitial plane, adjusting the size of the wire loop end effector as needed to navigate the artery and dissect a plaque column, until the end of the plaque is reached. The wire loop end effector is then used as a plaque cutter to transect the distal end of the plaque column. The endarterectomy device is further configured along its length with support arms that facilitate removal of the plaque column as the device is removed from the artery.

20 Claims, 5 Drawing Sheets

(51) Int. Cl.
*A61B 90/00* (2016.01)
*A61B 17/00* (2006.01)
*A61B 17/3205* (2006.01)
*A61B 18/14* (2006.01)

(56) References Cited

U.S. PATENT DOCUMENTS

| | | | |
|---|---|---|---|
| 2006/0229600 A1* | 10/2006 | Canady | A61B 18/14 606/49 |
| 2007/0027456 A1* | 2/2007 | Gartner | A61B 17/221 606/113 |
| 2010/0042107 A1* | 2/2010 | Merrifield | A61B 17/221 606/127 |
| 2014/0276908 A1* | 9/2014 | Raybin | A61B 18/149 606/113 |
| 2014/0378988 A1* | 12/2014 | Raybin | A61B 17/221 606/113 |
| 2015/0119884 A1* | 4/2015 | Fung | A61B 17/12013 606/41 |
| 2015/0173783 A1* | 6/2015 | Tah | A61B 17/221 606/127 |
| 2015/0297256 A1* | 10/2015 | Galer | A61B 17/32056 606/190 |
| 2016/0166270 A1* | 6/2016 | Hera | A61B 17/221 606/127 |
| 2016/0278797 A1* | 9/2016 | Rohan | A61B 17/221 |
| 2016/0346002 A1* | 12/2016 | Avneri | A61B 17/32056 |

* cited by examiner

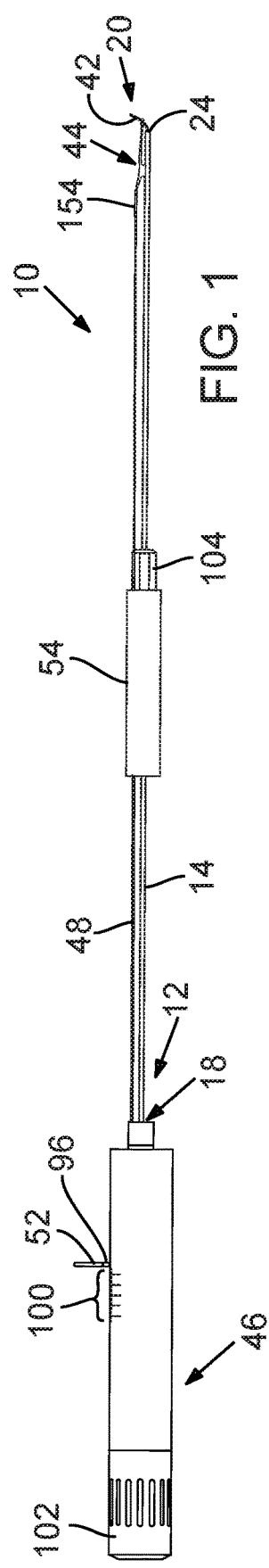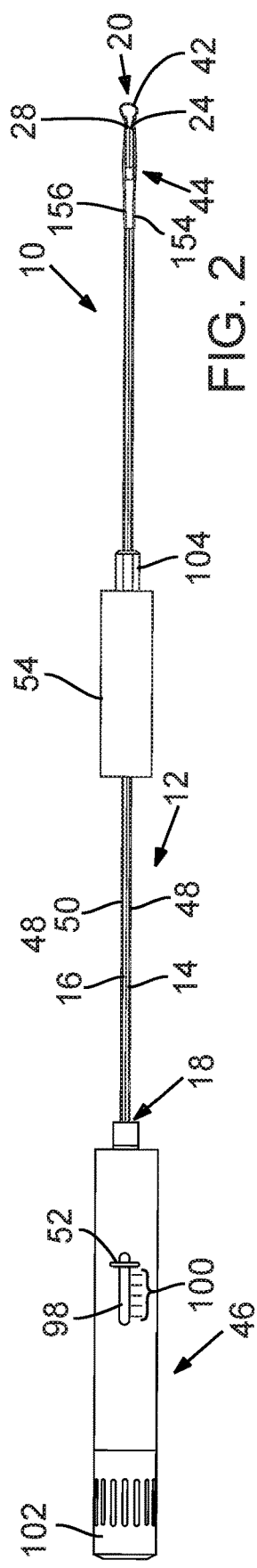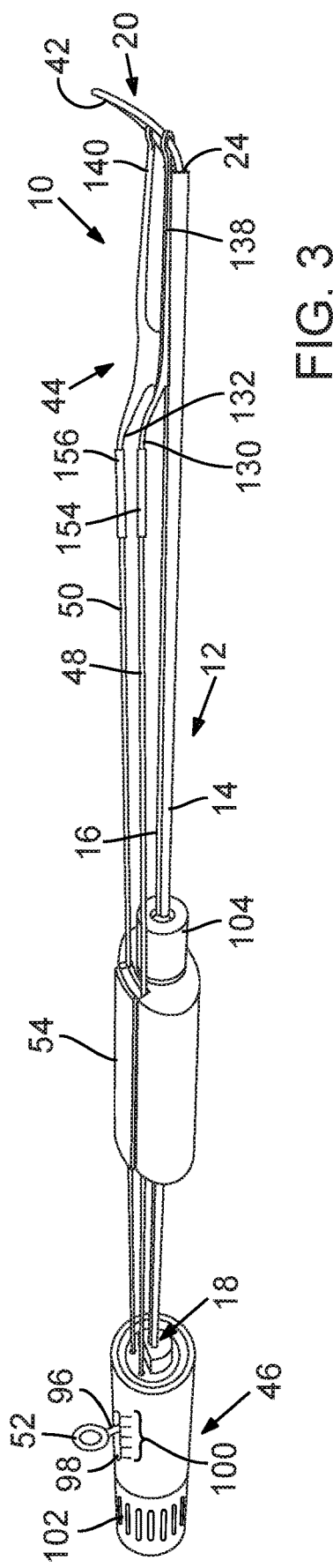

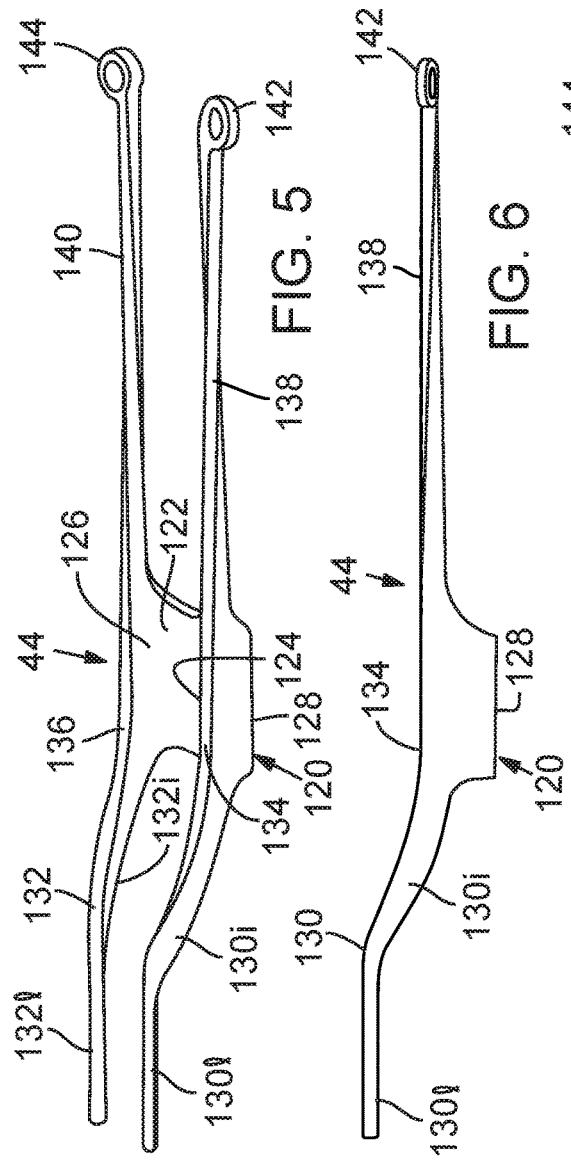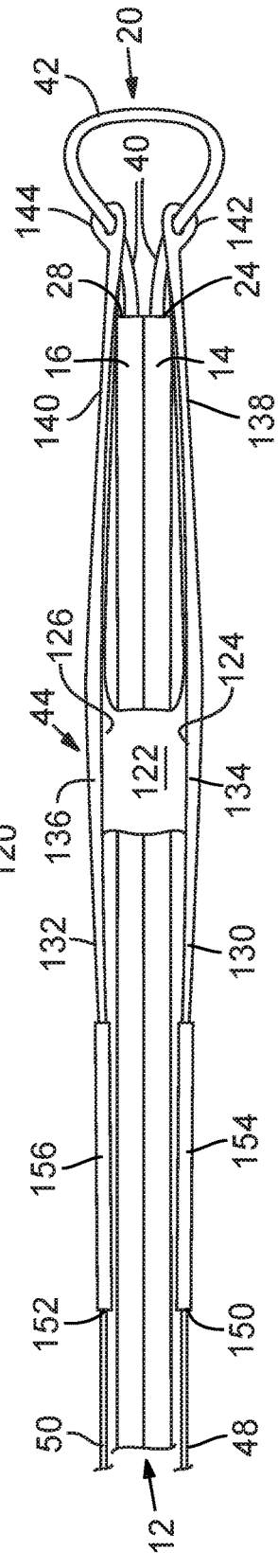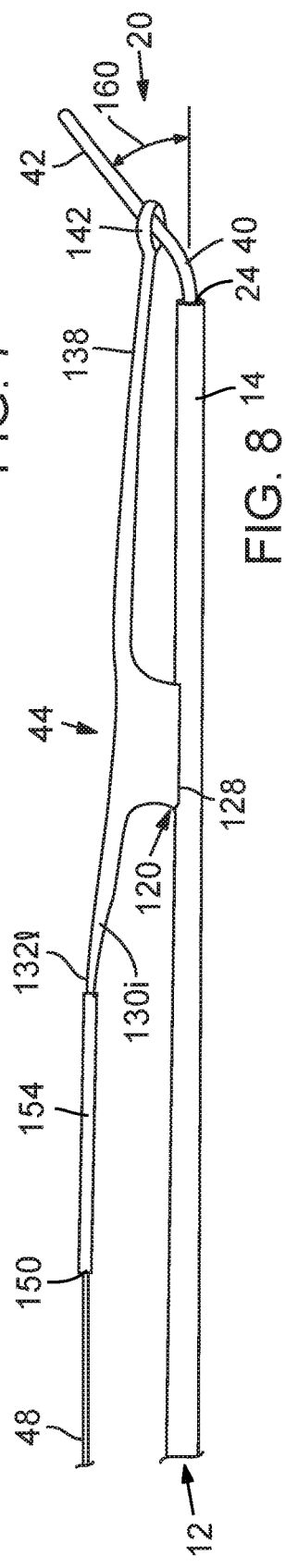

ENDARTERECTOMY DEVICE

RELATED APPLICATION

This application claims benefit of U.S. Patent Application No. 62/824,896, filed Mar. 27, 2019, which is incorporated by reference in its entirety herein.

FEDERALLY SPONSORED RESEARCH OR DEVELOPMENT

This invention was made with government support under TR000128 awarded by the National Institutes of Health. The government has certain rights in the invention.

COPYRIGHT NOTICE

©2020 Oregon Health & Science University. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

TECHNICAL FIELD

This disclosure relates generally to surgical devices and, more specifically, to an endarterectomy device with a wire loop end effector.

BACKGROUND INFORMATION

Peripheral artery disease (PAD) is a condition characterized by the narrowing or occlusion of segments of arteries that results in compromised blood flow to the limbs. PAD is commonly caused by a buildup of plaques deposited in the inner layer, or intima, of the artery wall in contact with blood flow. These plaques are comprised of cholesterol, fatty substances, calcium depositions, and cellular waste products. As plaque builds up, the wall of the blood vessel thickens, narrowing the channel within the artery, reducing blood flow, and, consequently, reducing the amount of oxygen and other nutrients reaching the peripheral body. The shape of the plaque occlusions may also vary such that the channel may be partly or totally occluded at sites along the length of diseased artery.

Remote endarterectomy is a minimally invasive surgical procedure performed to remove the diseased intima and adhered plaque from an occluded artery, thereby restoring blood flow through the affected artery segment. In a remote endarterectomy procedure, a single longitudinal incision is used to establish an entry point into the proximal end of an occluded artery segment, and a circumferential dissection plane is initiated between the plaque/intima core and the outer layer, or adventia, of the artery segment. A blunt dissection of the diseased core from the surrounding advential tissue is performed using a stripper tool with an annular or semiannular profile, advancing the tool's leading edge longitudinally along the artery to separate the intima/plaque from the adventia. Once the leading edge has been advanced sufficiently to the end artery segment to detach the diseased intimal portion, the distal end of the cleaved intimal layer is severed and the cylindrical core comprising the dissected intima and encapsulated plaque is removed en bloc from the artery lumen. In some cases, a stent may be deployed at the distal site where the cleaved intimal layer was severed to "tack down" the plaque and to prevent a flap from obstructing the lumen.

While remote endarterectomy is a viable and durable procedure, there are problems with current endarterectomy tools and devices. For example, the stripper tool used to perform the circumferential dissection typically has a fixed diameter or shape, requiring that a range of tool sizes be available for selection during the procedure. In addition, tool rigidity may cause perforation of the adventia as the leading edge is advanced during the procedure and may not be amenable to navigating around calcified or irregularly shaped plaques. And once dissection of the plaque/intima from the adventia is completed, a different tool may be required to grasp and extract the diseased core from the lumen. As such, there is a need for new devices for remote endarterectomy to address these problems.

SUMMARY OF THE DISCLOSURE

An endarterectomy device for performing remote endarterectomy procedures is disclosed. The endarterectomy device comprises a spline having proximal and distal ends, the spline including two tubular sheaths extending side by side along the length of the spline, each sheath having openings at their respective proximal and distal ends. The proximal end of the spline is operatively connected to a control handle to support the two sheaths.

A spring assembly is connected to the spline near its distal end. The spring assembly includes a base portion attached to the spline, two spaced-apart proximal spring support arms extending toward the proximal end of the spline, and two spaced-apart distal spring support arms extending beyond the distal end of the spline. Each of the distal spring support arms terminates in a respective ring. The two spaced-apart proximal spring support arms are connected to, respectively, two assembly support arms that extend proximally to connect to the control handle.

A length of wire is disposed within the two sheaths of the spline and is oriented so that the free ends of the wire emerge from the proximal end openings of the sheaths. These free ends of the wire are operatively coupled to a wire loop control integrated into the control handle of the device. The wire loop control is configured to allow a user to manually translate the wire proximally or distally within the sheaths of the spline. In some embodiments, the control handle may further comprise a locking mechanism which, when engaged, restricts translation of the wire proximally or distally. At the distal end of the spline, a section of the wire protrudes from the distal end openings of the sheaths and passes through the rings situated at the ends of the distal spring support arms. This section of wire configures a wire loop end effector that extends beyond the distal end of the spline. By manipulating the wire loop control, the user can vary the size of the wire loop end effector.

In some embodiments, the base portion of the spring assembly is in the form of a tubular segment having an arcuate inner surface and opposed side portions that form a cradle that is open-ended along the length of the spline. In this spring assembly embodiment, the two spaced-apart proximal spring support arms extend from their respective side portions toward the proximal end of the spline, and the two spaced-apart distal spring support arms extend from their respective side portions toward the distal end of the spline.

In some embodiments, the endarterectomy device may also comprise a proximal handle positioned between the loop control and the distal end of the spline. In embodiments, the proximal handle is configured to be movable for selective positioning along the length of the spline. The proximal handle may also comprise a locking mechanism that can be used to immobilize the proximal handle in place, once it has been moved to a desired position.

Additional aspects and advantages will be apparent from the following detailed description of preferred embodiments, which proceeds with reference to the accompanying drawings.

BRIEF DESCRIPTION OF THE DRAWINGS

FIGS. 1, 2, and 3 are diagrams showing, respectively, side elevation, top plan, and perspective views of a remote endarterectomy device, according to one embodiment.

FIGS. 5 and 6 are diagrams showing, respectively, perspective and side elevation views of an embodiment of a spring assembly for the disclosed endarterectomy device in which a base portion of the spring assembly forms a cradle.

FIGS. 7 and 8 are diagrams showing, respectively, fragmentary top plan and side elevation views of the distal end of an endarterectomy device constructed with the spring assembly of FIGS. 5 and 6.

DETAILED DESCRIPTION OF PREFERRED EMBODIMENTS

Figure 4:
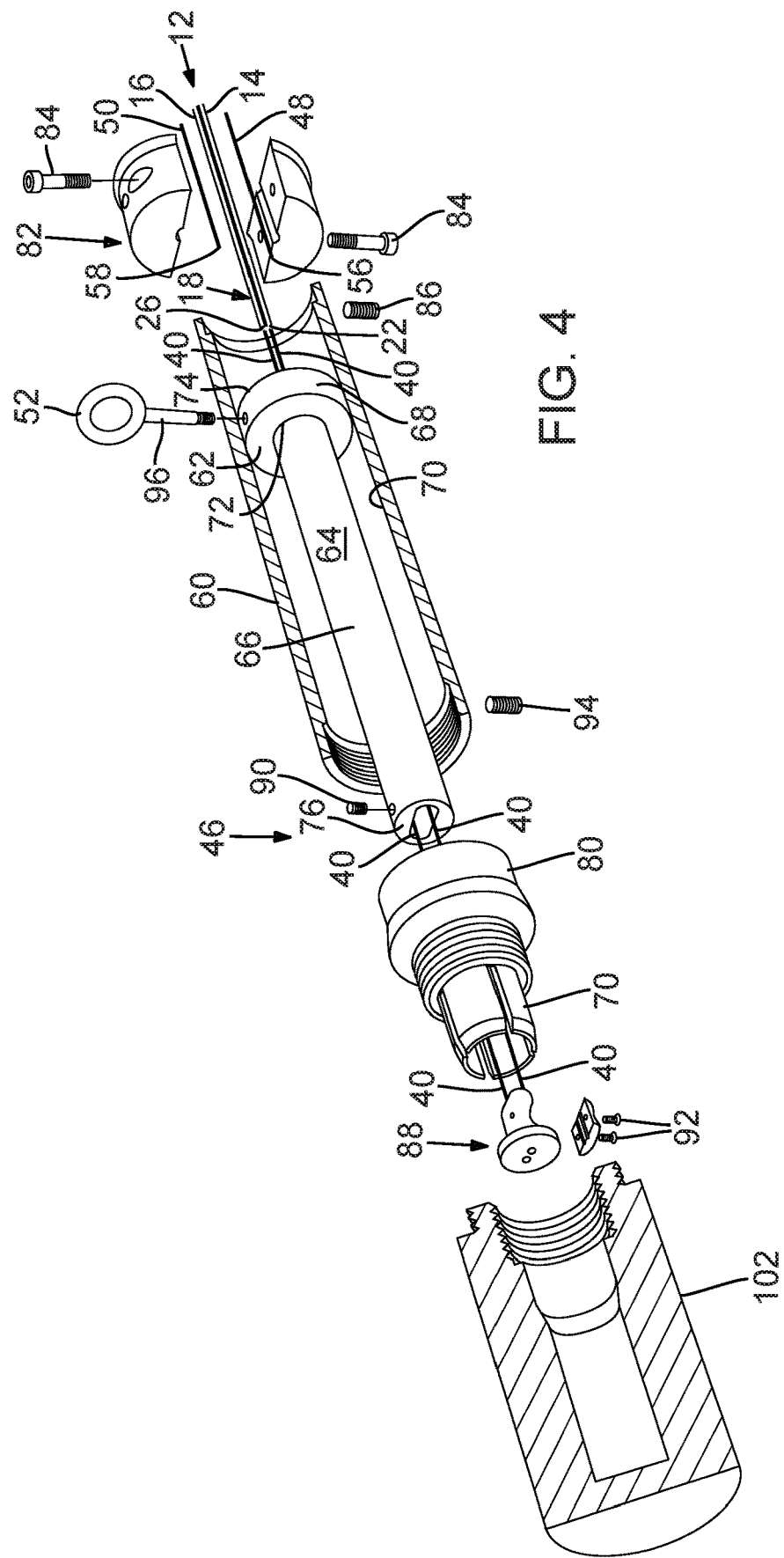
FIG. 4 is an exploded view showing partly in cross section a control handle of the endarterectomy device of FIGS. 1-3.

Various embodiments of the disclosed endarterectomy device implemented with a wire loop end effector are adjustable to accommodate changes in arterial and plaque size. By virtue of its adjustable nature, the disclosed endarterectomy device can better remove irregular or calcified plaque and occluded stents than previously designed endarterectomy devices. FIGS. 1, 2, and 3 show side elevation, top plan, and perspective views of an endarterectomy device 10, according to one embodiment.

Endarterectomy device 10 includes a spline 12 that is constructed from two sheaths, or hollow tubes, 14 and 16 extending side by side along the length of spline 12. Spline 12 has a proximal end 18 and a distal end 20. Sheaths 14 and 16 may be coupled to each other along their lengths. Sheath 14 has a proximal end opening 22 (FIG. 4) and a distal end opening 24, and sheath 16 has a proximal end opening 26 (FIG. 4) and a distal end opening 28. Spline 12 includes, at its distal end 20, a guide wire 40 that is disposed within sheaths 14 and 16. An exposed wire section 42 of guide wire 40 emerges from distal end openings 24 and 28 of the respective sheaths 14 and 16. Wire section 42 cooperates with spring assembly 44 to configure a wire loop end effector of variable size that extends beyond distal end 20 of spline 12. (The terms "wire section" and "wire loop end effector" are used interchangeably throughout.) Spline 12 includes, at its proximal end 18, a control handle 46 that supports sheaths 14 and 16 and assembly support arms 48 and 50. Assembly support arms 48 and 50 are operatively connected to spring assembly 44 and extend between control handle 46 and spring assembly 44 to form, together with wire loop end effector 42 and outer surfaces of sheaths 14 and 16, a cage in which plaque detached from a subject's artery can lie during extraction of spline 12. A wire loop control 52 housed in control handle 46 provides user operational control to vary the size of wire loop end effector 42. In certain embodiments, a lockable proximal handle 54 encompasses spline 12 and assembly support arms 48 and 50. Proximal handle 54 is slidable along spline 12 between control handle 46 and distal end 20 of spline 12 and, while in a locked position, allows a user to drive spline 12 and wire loop end effector 42 further into a subject's artery.

In embodiments, spline 12 extends distally from wire loop control 52 toward the distal end of endarterectomy device 10. Spline 12 is made up of at least two sheaths, the embodiment of endarterectomy device 10 shown in FIGS. 1-3 having sheaths 14 and 16 of substantially the same lengths. In embodiments, spline 12 is configured to allow free movement of guide wire 40 within either one or both of sheaths 14 and 16, for example so that guide wire 40 can be moved back and forth axially within sheaths 14 and 16. Spline 12 can be made of any material that is sufficiently strong and flexible to resist axial forces and not bend or buckle when proximal handle 54 is used. Spline 12 will bend in any direction along its length that is inserted into an artery, for example to follow the contour of the artery, which is rarely uniformly straight. The tubes comprising sheaths 14 and 16 can be adhered by any appropriate method, including use of adhesive, welds (including skip welds), or be formed as a single piece from plastic or other material. In certain embodiments, spline 12 comprises two round metal tubes adhered to each other side by side. In embodiments, sheaths 14 and 16 are coupled together by one or more skip welds, for example every 6 inches along their lengths. Use of skip welds readily accommodates bending forces exerted against sheaths 14 and 16. The length of spline 12 can be between about 15 inches and about 25 inches, for example, 20 inches.

Assembly support arms 48 and 50 are formed of lengths of metal alloy such as Nitinol, metal such as stainless steel, or plastic material. Assembly support arms 48 and 50 are maintained substantially parallel to each other along the length of spline 12 and substantially equidistant from spline 12. Assembly support arms 48 and 50 are flexible but sufficiently stiff to form, together with spring assembly 44, spline 12, and wire loop end effector 42, the cage for holding a plaque column that is dissected from a subject's blood vessel. Together with spline 12, assembly support arms 48 and 50 provide three points of lengthwise contact with the plaque column. Accordingly, assembly support arms 48 and 50 and spline 12 facilitate the containment and extraction of a dissected plaque column during a remote endarterectomy procedure.

FIG. 4 is an exploded view showing partly in cross section control handle 46, which contains sliding wire loop control 52 and secures spline 12 at its proximal end 18, the ends of guide wire 40, and proximal ends 56 and 58 of the respective assembly support arms 48 and 50. Control handle 46 includes a cylindrical housing 60, the interior of which contains a collar 62 that is fitted on an outer surface 64 of a hollow shaft 66 that extends along the length of housing 60. Collar 62 has an outer surface 68 that slides along an inner surface 70 of housing 60. Hollow shaft 66, at its distal end 74, terminates in collar 62, and, at its proximal end 76, terminates in a locking collet device 78. Locking collet device 78 has a cylindrical base 80 that fits in housing 60 by threaded engagement.

A first two-piece clamp 82 fitted within housing 60 at its distal end secures spline 12 and assembly support arms 48 and 50 to control handle 46. Screws 84 hold together the two pieces of first clamp 82, which is secured to housing 60 of control handle 46 by a set screw 86. A second two-piece clamp 88 fitted within hollow shaft 66 at its proximal end 76 secures the two ends of guide wire 40. A set screw 90 secures second clamp 88 to hollow shaft 66. Screws 92 hold together the two pieces of second clamp 88, which is secured to hollow shaft 66 by a set screw 94.

Wire loop control 52 in the form of an eye screw includes a threaded shaft 96 that passes through collar 62 for threaded engagement with hollow shaft 66. A slot 98 (FIGS. 2 and 3) provided in housing 60 establishes a travel distance along which a user can slide wire loop control 52 back and forth axially to adjust the size of wire loop end effector 42, as proximal end 76 of hollow shaft 66 moves within locking collet device 78. Housing 60 has on its outer surface indicator marks 100 that indicate to the user whether and to what degree wire loop end effector 42 is open (extended) or closed (retracted). In an alternative implementation, wire loop control 52 may be configured to stop at a plurality of predetermined points that correspond to predetermined sizes of wire loop end effector 42.

A cylindrical knob 102 fits over locking collet device 78 for threaded engagement to regulate wire loop end effector freedom of movement. For example, one-half turn of knob 102 would lock in place hollow shaft 66 and prevent movement of wire loop control 52.

Wire loop control 52 is configured to allow a user to increase and decrease the size of wire loop end effector 42 at the distal end of endarterectomy device 10. Movement of wire loop control 52 toward the distal end of endarterectomy device 10 extends guide wire 40 and increases the size of wire section 42 forming the wire loop end effector, and movement of wire loop control 52 toward the proximal end of endarterectomy device 10 retracts guide wire 40 and decreases the size of the wire loop end effector. The reverse configuration is also contemplated for other embodiments, as are other methods of effecting the size of wire loop end effector 42, such as by twisting the wire loop control, or having a wire loop control driven by an electric motor.

Wire loop control 52 can be in communication with guide wire 40 via any known mechanism. In some embodiments, activation of wire loop control 52 can cause a motor (such as a battery-powered motor) to feed guide wire 40 through endarterectomy device 10 to increase or decrease the size of wire loop end effector 42. Wire loop control 52 can be of any appropriate style or shape such as a ring, barrel, dial, ball, toggle switch, rocker switch (or any bidirectional switch), joystick, button, wheel, or any combinations or multiples of these or other directional controllers. Housing 60 can be made of any appropriate material, including computer machine control (CNC)-plastic, metal, or glass.

The embodiment of endarterectomy device 10 shown in FIGS. 1-3 includes proximal handle 54, which glides along spline 12 and guides and orients assembly support arms 48 and 50. Proximal handle 54 is configured to unlock, be directed by the user to the distal end 20 of spline 12, lock, and thereby drive wire loop end effector 42 and spline 12 further into a subject's artery. A one-half turn, dual tube collet 104 grips spline 12 to lock proximal handle 54 at a user's desired location. Alternatively, proximal handle 54 can be locked and unlocked by means of a ratchet or other similar mechanism. Proximal handle 54 is preferably made of CNC-machined plastic in an ergonomic shape that facilitates grip and maneuverability for the user.

FIGS. 5 and 6 are, respectively, perspective and side elevation views of spring assembly 44. Spring assembly 44 includes a structurally stable base portion 120 in the form of a tubular segment having an arcuate inner surface 122 and opposed arcuate side portions 124 and 126. Inner surface 122 is preferably of cylindrical shape. Base portion 120 forms a cradle that is open-ended along the length of spline 12. Base portion 120 has an exterior bottom surface 128 that is wide and generally flat to make it compatible for attachment by welding or other suitable bonding method to the outer surfaces of sheaths 14 and 16 of spline 12.

Proximal spring support arms 130 and 132 connected to upper side margins 134 and 136 of respective side portions 124 and 126 of base portion 120 extend in a direction toward the proximal end of endarterectomy device 10. Proximal spring support arms 130 and 132 include respective inclined portions 130*i* and 132*i* that project at an angle proximally upward and away from exterior bottom surface 128 and respective level portions 130I and 132I that are generally parallel to sheaths 14 and 16 when base portion 120 is attached to them.

Distal spring support arms 138 and 140 connected to upper side margins 134 and 136 of respective side portions 124 and 126 extend in a direction toward the distal end of endarterectomy device 10. Distal spring support arms 138 and 140 terminate in rings 142 and 144, respectively. Rings 142 and 144 are of sufficient internal diameter to allow free movement of guide wire 40 through them. Distal spring support arms 138 and 140 are tapered and of short length that is sufficient to impart stability to wire loop end effector 42. Level portions 130I and 132I of respective proximal spring support arms 130 and 132 are parallel to each other and to sheaths 14 and 16. Distal spring support arms 138 and 140 are parallel to each other and to sheaths 14 and 16, and parallel to but offset from level portions 130I and 132I a distance proximally downward toward base portion 120.

Spring assembly 44 including base portion 120, proximal spring support arms 130 and 132, and distal spring support arms 138 and 140 is preferably a unitary component part formed from laser-cut Nitinol (nickel and titanium) metal alloy. Spring assembly 44 may alternatively be made of other suitable material that meets mechanical specification requirements, including a plastic or other organic compound-based material, a carbon fiber-based material, or a metal such as aluminum.

FIGS. 7 and 8 are, respectively, fragmentary top plan and side elevation views of the distal end of endarterectomy device 10 constructed with spring assembly 44 to form wire loop end effector 42. Proximal spring support arms 130 and 132 are positioned at a greater distance vertically away from base portion 120 than the distance of distal spring support arms 138 and 140 from base portion 120 such that proximal spring support arms 130 and 132 are in-line with assembly support arms 48 and 50 emerging from proximal handle 54 when base portion 120 is coupled to spline 12. Proximal spring support arms 130 and 132 are coupled to distal ends 150 and 152 of assembly support arms 48 and 50, respectively. Coupling of proximal spring support arms 130 and 132 is preferably achieved by use of weld tubes 154 and 156, respectively. Guide wire section 42 emerges from distal end openings 24 and 28 of sheaths 14 and 16, respectively. Distal spring support arms 138 and 140 are positioned at a height vertically away from base portion 120 such that, when base portion 120 is coupled to spline 12, wire loop end effector 42 of guide wire 40 passes through rings 142 and 144 at the distal ends of distal spring support arms 138 and 140, respectively. Distal spring support arms 138 and 140 extend beyond distal end openings 24 and 28 of the respective sheaths 14 and 16 by a distance that causes guide wire section 42 passing through rings 142 and 144 to form and hold the wire loop end effector at about a 45° angle 160.

Figure 9A:
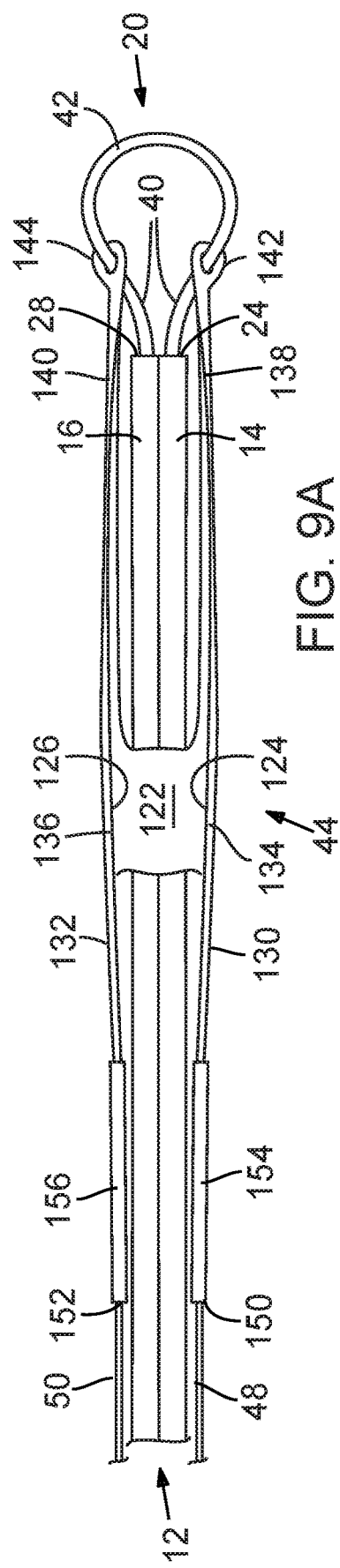
FIG. 9A is a diagram showing a top plan view of the distal end of the disclosed endarterectomy device in which the wire loop end effector is deployed in an extended position.
Figure 9B:
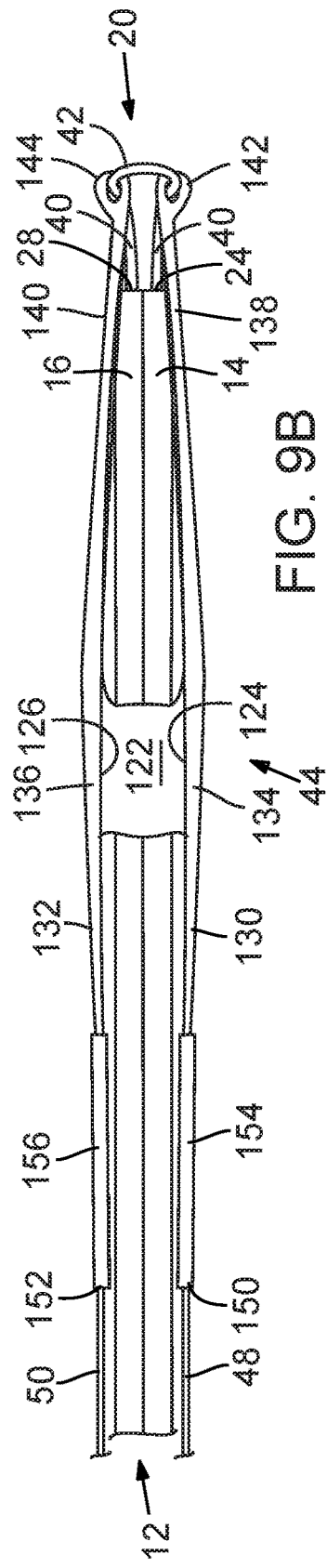
FIG. 9B is a diagram showing a top plan view of the distal end of the disclosed endarterectomy device in which the wire loop end effector is deployed in a retracted position.

FIGS. 9A and 9B show the different lateral distances separating distal spring support arms 138 and 140 as a user of endarterectomy device 10 slides wire loop control 52 on control handle 46 to different positions to vary the size of wire loop end effector 42. FIG. 9A shows wire loop end effector 42 in a partly extended state, resulting from wire loop control 52 at its midway position between the forward-most and rearward-most positions on control handle 46. Wire loop end effector 42 in its partly extended state draws distal spring support arms 138 and 140 apart from each other so that the center-to-distance separating their respective rings 142 and 144 is about a maximum center-to-distance between them. FIG. 9B shows wire loop end effector 42 in its fully retracted state, resulting from wire loop control 52 at its rearward-most position toward the proximal end of endarterectomy device 10. Wire loop end effector 42 in its fully retracted state draws distal spring support arms 138 and 140 together so that the center-to-distance separating their respective rings 142 and 144 is slightly larger than the center-to-distance between distal end openings 24 and 28 of sheaths 14 and 16, respectively. FIGS. 9A and 9B demonstrate that the portions of wire section 42 of guide wire 40 emerging from distal end openings 24 and 28 of the respective sheaths 14 and 16 expand and contract in unison to provide wire loop end effector 42 of different sizes that are substantially symmetrical about the longitudinal axis of endarterectomy device 10.

During a remote endarterectomy procedure, wire loop end effector 42 provides the cutting action of endarterectomy device 10. To effect dissection of plaque from an artery wall, wire loop end effector 42 is forced through the plaque and tissue comprising the subadvential endarterectomy plane, engendering both axial and bending loads within wire loop end effector 42 and within the structures comprising the distal end of endarterectomy device 10, including spring assembly 44. With reference to FIG. 8, spring assembly 44 is positioned on spline 12 so that rings 142 and 144 engage wire loop end effector 42 and maintain it at an approximately 45° angle 160. Accordingly, the distal-most apex of wire loop end effector 42 serves as the leading edge to separate plaque from the artery wall, and as such is constructed of an appropriate material of sufficient diameter and stiffness to be advanced without "bowing back" under load. Similarly, spring assembly 44 is designed according to mechanical specification requirements to confer sufficient mechanical stability as load is transmitted from wire loop end effector 42 to distal spring support arms 138 and 140 to maintain wire loop end effector 42 at an approximately 45° angle 160 during use.

Wire loop end effector 42 can be constructed of any mechanically suitable material including a plastic or other organic compound-based material, a carbon fiber-based material, or a metal alloy such as Nitinol. The wire comprising wire loop end effector 42 may include a plastic, polymeric, biological, or other coating such as TEFLON®. The wire comprising wire loop end effector 42 can also be of any appropriate gauge to confer sufficient mechanical behavior in combination with spring assembly 44 and other load-bearing components of endarterectomy device 10. In embodiments, wire loop end effector 42 comprises a metal alloy such as Nitinol having a gage diameter between about 0.018 inch and about 0.036 inch, for example a Nitinol wire of 0.024-inch diameter. In still further examples, wire loop end effector 42 comprises a coating such as TEFLON®.

Figure 10:
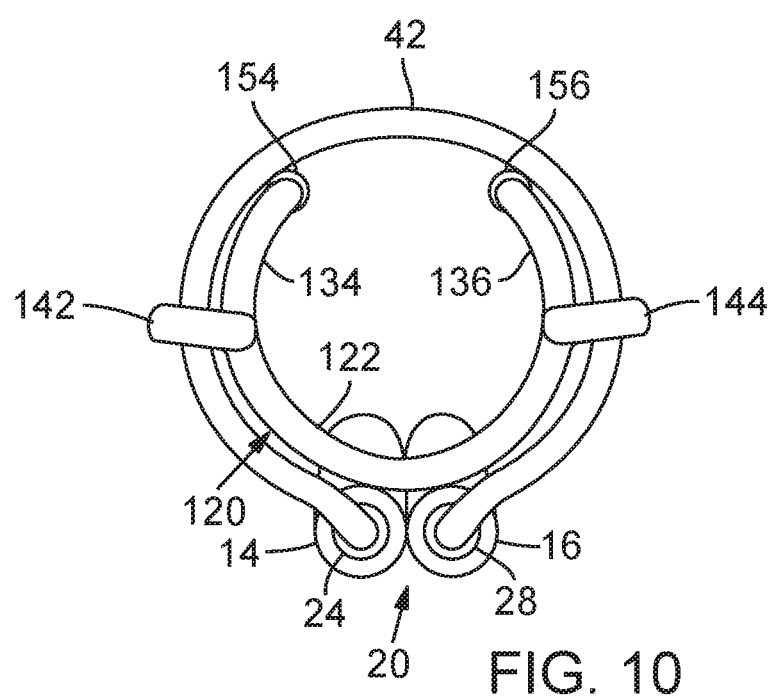
FIG. 10 is a frontal view of the distal end of the disclosed endarterectomy device showing that the frontal projection of the wire loop end effector and base portion of the spring assembly forms a cleaving plane having a circular profile.

FIG. 10 is a frontal view of the distal end of endarterectomy device 10, showing that the frontal projection of wire loop end effector 42 and base portion 120 of spring assembly 44 forms a cleaving plane having a circular profile as it as advanced along the subadvential space of an artery. This circular profile ensures that, as the distal end of the endarterectomy device 10 is advanced along the length of the subject's artery during an endarterectomy procedure, the dissected plaque maintains an essentially columnar shape. As dissection proceeds and the length of the plaque column increases, it is fed into and is retained by the cradle enclosure formed at the distal end and extending along the length of endarterectomy device 10. This cradle enclosure is generally defined on its underside by sheaths 14 and 16 and arcuate inner surface 122 of base portion 120 of spring assembly 44, and on its lateral sides by upper side margins 134 and 136. As dissection further proceeds and the plaque column lengthens beyond spring assembly 44, the plaque column is delivered into the cage formed by wire loop end effector 42, sheaths 14 and 16 of spline 12, and assembly support arms 48 and 50.

The following describes methods of performing remote endarterectomy procedures using endarterectomy device 10 on a subject. In general, methods of use of endarterectomy device 10 entail establishing an endarterectomy plane in the subadventitial space of an artery, dissecting a plaque along the wall of an artery, transecting the end of a dissected plaque, and facilitating plaque removal from the subject. The disclosed methods are applicable to performing remote endarterectomy in segments of occluded arteries of variable length. In some applications, for example, the disclosed methods may be used to remove plaque from an entire length of a superficial femoral artery. The plaque may include a stent, calcified plaque, irregular plaque, or diseased intima.

More specifically, the methods of removing plaque from a subject's blood vessel such as an artery entail: advancing, along a subadventitial plane of the blood vessel, endarterectomy device 10 having at its distal end a wire loop end effector 42, thereby dissecting a plaque column from the blood vessel wall; retracting wire loop end effector 42 to a closed (retracted) configuration, thereby transecting the distal end of the plaque column separating it from the blood vessel; and removing endarterectomy device 10 in tandem with the dissected plaque column from the blood vessel, thereby removing the plaque from the blood vessel. The methods may further entail use of a live imaging system such as fluoroscopy during the procedure.

Endarterectomy device 10 is designed with features for navigating occluded arteries and accommodating calcified or irregular plaque or variations in artery diameter. Endarterectomy device 10 has control handle 46 configured with wire loop control 52 that may be manipulated by the user's thumb to allow continual active adjustment of the size of wire loop end effector 42 to facilitate passage down an irregularly shaped plaque or an artery of variable diameter. Wire loop control 52 also allows wire loop end effector 42 to be completely retracted to transect the plaque to fully separate it from the artery wall. Control handle 46 is further configured with a locking mechanism comprising locking collet device 78 that may be engaged by rotating knob 102 to constrain wire loop end effector 42 at a constant size.

Endarterectomy device 10 may also be configured with proximal handle 54 to facilitate control and advancement of the device during remote endarterectomy procedures. Proximal handle 54 may be employed to facilitate the pushing of distal end 20 of spline 12 into an artery to advance the dissection path of wire loop end effector 42 along the artery wall in the subadvential space. Proximal handle 54 may be movable for adjustable positioning along the length of spline 12 and may further be locked in position on spline 12 using one-half turn, dual tube collet 104. In typical use, the user may hold locked proximal handle 54 with one hand near the site of vessel entry, allowing the user to push a length of spline 12 into the vessel. As advancement along the vessel proceeds, proximal handle 54 may be unlocked, repositioned more proximally along spline 12, and then re-locked, to allow additional length of spline 20 to be fed into the artery. Accordingly, when it is configured with proximal handle 54, endarterectomy device 10 may be operated with two hands: one hand on control handle 46 adjusting the size of wire loop end effector 42, and the other hand on proximal handle 54 pushing the device forward. The user may repeat the steps of guiding spline 12 into the artery and adjusting the position of proximal handle 54 until wire loop end effector 42 has reached the desired endpoint of dissection. Wire loop control 52 may then be adjusted to fully retract wire loop end effector 42 into spline 12, thereby transecting the plaque column and separating it from the artery wall. After the plaque has been transected, the dissected column of plaque lies on spline 12 and is in contact with first and second assembly support arms 48 and 50 along the column length. This longitudinal contact with the plaque column facilitates its complete removal when endarterectomy device 10 is backed out of the artery.

Endarterectomy device 10 may also be used to remove plaque from an entire length of a superficial femoral artery. Proximal handle 54 of device 10 may be positioned and locked near the distal end of endarterectomy device 10, near spring assembly 44, so that it may be held by the user to guide the wire loop end effector 42 into the superficial femoral artery and perform an initial dissection of plaque along the subadvential plane. To advance wire loop end effector 42 of device 10 further along the artery, proximal handle 54 may be unlocked, slidably re-positioned closer to control handle 46, and re-locked into position. The user repeats the steps of guiding wire loop end effector 42 of device 10 into the superficial femoral artery and adjusting the position of proximal handle 54 toward control handle 46, which adjustment may continue with proximal handle 54 making contact with control handle 46, until the wire loop end effector 42 reaches the distal end of the superficial femoral artery. Wire loop control 52 may then be used to retract wire loop end effector 42 into spline 12, thereby transecting the plaque at the distal end of the superficial femoral artery. Endarterectomy device 10 is then removed from the artery, carrying with it the plaque that has been dissected from the adventia along the entire length of the lumen.

It will be obvious to those having skill in the art that many changes may be made to the details of the above-described embodiments without departing from the underlying principles of the invention. The scope of the present invention should, therefore, be determined only by the following claims.

The invention claimed is:
1. An endarterectomy device, comprising:
   a spline having a length and proximal and distal ends, the spline including first and second sheaths extending side by side along the length of the spline, and each of the first and second sheaths having a proximal end opening at the proximal end of the spline and a distal end opening at the distal end of the spline;
   a spring assembly operatively connected to the spline near its distal end, the spring assembly including a base portion that is operatively connected to first and second spaced-apart proximal spring support arms and to first and second spaced-apart distal spring support arms, the first and second spaced-apart proximal spring support arms extending toward the proximal end of the spline, and the first and second spaced-apart distal spring support arms extending toward the distal end of the spline, the first and second distal spring support arms terminating in respective first and second rings at locations beyond the distal end of the spline;
   first and second assembly support arms having respective first and second proximal ends and respective first and second distal ends, the first and second distal ends of the first and second assembly support arms joined to the respective first and second proximal spring support arms;
   a guide wire disposed within, and having first and second ends emerging from the proximal end openings of, the first and second sheaths;
   a section of the guide wire protruding from the distal end openings of the first and second sheaths and passing through the first and second rings to configure a wire loop end effector of variable size beyond the distal end of the spline;
   a wire loop control positioned near or at the proximal end of the spline and operatively coupled to the first and second ends of the guide wire to vary the size of the wire loop end effector; and
   a control handle operatively connected to the proximal end of the spline to support the first and second sheaths at the proximal end of the spline and the proximal ends of the first and second assembly support arms.

2. The endarterectomy device of claim 1, in which the base portion of the spring assembly is in the form of a tubular segment having an arcuate inner surface and includes first and second opposed side portions to form a cradle that is open-ended along the length of the spline, and in which the first and second spaced-apart proximal spring support arms extend from the respective first and second side portions toward the proximal end of the spline, and the first and second spaced-apart distal spring support arms extend from the respective first and second side portions toward the distal end of the spline.

3. The endarterectomy device of claim 1, further comprising a proximal handle positioned between the wire loop control and the distal end of the spline.

4. The endarterectomy device of claim 3, in which the proximal handle is movable for selective positioning along the length of the spline.

5. The endarterectomy device of claim 1, in which the wire loop control is operatively connected to the control handle and is configured to move the guide wire along the length of the spline and stop at user-selected points that correspond to different sizes of the wire loop end effector.

6. The endarterectomy device of claim 1, in which the guide wire comprises a metal alloy.

7. The endarterectomy device of claim 6, in which the metal alloy includes Nitinol.

8. The endarterectomy device of claim 1, in which the section of wire comprises a coating.

9. The endarterectomy device of claim 8, in which the coating includes TEFLON® material.

10. The endarterectomy device claim 1, in which the wire loop control is configured to reversibly stop movement of the wire within the spline and thereby maintain the size of the loop.

11. The endarterectomy device of claim 1, in which the first and second assembly support arms include lengths of metal alloy, metal wire, or plastic material.

12. A method of removing a plaque from a blood vessel of a subject, comprising:
- inserting the distal end of the spline of the endarterectomy device of claim 1 into a lumen of the blood vessel;
- adjusting the wire loop control to form the wire loop end effector in an extended position aligned with a subadventitial plane;
- advancing the wire loop end effector along the subadventitial plane, thereby dissecting the plaque from the blood vessel;
- adjusting the wire loop control to return the wire loop end effector to the retracted position to transect the plaque and thereby form a transected portion of plaque lying on the spline; and
- removing from the blood vessel the spline and the transected portion of plaque lying on the spline.

13. The method of claim 12, in which the blood vessel comprises an artery.

14. The method of claim 12, in which the plaque comprises an occluded stent.

15. The method of claim 12, in which the plaque comprises a calcified plaque.

16. The method of claim 12, further comprising adjusting the control handle to maintain the size of the wire loop end effector while it is advancing along the subadventitial plane.

17. The method of claim 12, further comprising adjusting the control handle to vary the size of the wire loop end effector while advancing it along the subadventitial plane.

18. The method of claim 12, further comprising visualizing the blood vessel with live imaging system.

19. The method of claim 12, in which the endarterectomy device further comprises a proximal handle that may be movably positioned along the spline.

20. The method of claim 19, in which the advancing the wire loop end effector along the subadventitial plane comprises:
- positioning the proximal handle at a first location along the spline to delineate a first distal length of spline outside the blood vessel;
- pushing the first distal length of spline into the blood vessel using the proximal handle;
- re-positioning the proximal handle from the first location to a second location along the spline to delineate a second distal length of spline outside the blood vessel; and
- pushing the second distal length of spline into the blood vessel using the proximal handle.

* * * * *